(12) United States Patent
Baumgartner et al.

(10) Patent No.: US 11,040,861 B2
(45) Date of Patent: Jun. 22, 2021

(54) FILLING DEVICE FOR FILLING A CONTAINER TO BE FILLED WITH A FILLING PRODUCT IN A FILLING PRODUCT FILLING PLANT

(71) Applicant: KRONES AG, Neutraubling (DE)

(72) Inventors: Sebastian Baumgartner, Neutraubling (DE); Juergen Soellner, Neutraubling (DE); Thomas Weber, Neutraubling (DE); Thomas Knitl, Neutraubling (DE); Bernd Schafaczek, Neutraubling (DE)

(73) Assignee: KRONES AG, Neutraubling (DE)

( * ) Notice: Subject to any disclaimer, the term of this patent is extended or adjusted under 35 U.S.C. 154(b) by 0 days.

(21) Appl. No.: 16/467,899

(22) PCT Filed: Dec. 11, 2017

(86) PCT No.: PCT/EP2017/082197
§ 371 (c)(1),
(2) Date: Jun. 7, 2019

(87) PCT Pub. No.: WO2018/104551
PCT Pub. Date: Jun. 14, 2018

(65) Prior Publication Data
US 2020/0062566 A1 Feb. 27, 2020

(30) Foreign Application Priority Data
Dec. 9, 2016 (DE) .......................... 102016123965.8

(51) Int. Cl.
*B67C 3/22* (2006.01)
*B67C 3/00* (2006.01)
*A61L 2/07* (2006.01)

(52) U.S. Cl.
CPC ................ *B67C 3/001* (2013.01); *A61L 2/07* (2013.01); *B67C 3/007* (2013.01); *A61L 2202/23* (2013.01)

(58) Field of Classification Search
CPC . B67C 3/001; B67C 3/007; A61L 2/07; A61L 2202/23
See application file for complete search history.

(56) References Cited

U.S. PATENT DOCUMENTS 3,517,688 A 6/1970 Scholle
5,398,734 A * 3/1995 Hartel ...................... B08B 9/46
141/82

(Continued)

FOREIGN PATENT DOCUMENTS

CN 102372242 A 3/2012
EP 0590505 A1 4/1994

(Continued)

OTHER PUBLICATIONS

JP2004001850 machine translation, Jan. 8, 2004, all pages (Year: 2004).*

(Continued)

*Primary Examiner* — Nicholas A Arnett
(74) *Attorney, Agent, or Firm* — Maschoff Brennan

(57) ABSTRACT

The invention relates to a filling device for filling a container to be filled with a filling product in a filling product filling plant, comprising at least one filling valve for dosing the filling product into the container that is to be filled, as well as a sterilization device for sterilizing at least a portion of the at least one filling valve, wherein a contactless temperature sensor is provided for contactlessly measuring the temperature of the filling valve.

20 Claims, 2 Drawing Sheets

(56) References Cited

U.S. PATENT DOCUMENTS

| | | | | |
|---|---|---|---|---|
| 5,512,249 | A * | 4/1996 | Singh | A61L 2/07 137/241 |
| 8,968,645 | B2 * | 3/2015 | Euler | A61L 2/22 422/3 |
| 9,120,661 | B2 * | 9/2015 | Sangi | A61L 2/208 |
| 10,556,028 | B2 * | 2/2020 | Hayakawa | B08B 3/10 |
| 2005/0112040 | A1 * | 5/2005 | Hasegawa | A61L 2/24 422/300 |
| 2010/0147418 | A1 * | 6/2010 | Piana | G06K 5/00 141/98 |
| 2010/0276028 | A1 | 11/2010 | Sangi et al. | |
| 2012/0018030 | A1 * | 1/2012 | Laumer | B67C 3/001 141/1 |
| 2016/0121376 | A1 * | 5/2016 | Hayakawa | B08B 9/0325 422/3 |

FOREIGN PATENT DOCUMENTS

| | | |
|---|---|---|
| EP | 2409948 A2 | 1/2012 |
| EP | 3015418 A1 | 5/2016 |
| JP | 2004001850 A | 1/2004 |

OTHER PUBLICATIONS

First Office Action received in Chinese Application No. 201780086054.6, dated Sep. 2, 2020.

* cited by examiner

FILLING DEVICE FOR FILLING A CONTAINER TO BE FILLED WITH A FILLING PRODUCT IN A FILLING PRODUCT FILLING PLANT

TECHNICAL FIELD

The present invention relates to a filling device for filling a container to be filled with a filling product in a filling product filling plant, and a method for treating a filling device, preferably for cleaning and/or sterilizing the filling device.

BACKGROUND TO THE INVENTION

Filling devices for filling a container to be filled with a filling product, and methods for treating, in particular for cleaning and/or sterilizing, such filling devices are known from the state of the art.

It is known in filling product filling plants to fill containers or cans with beverages. For this purpose, filling elements are provided, which serve to fill containers with filling product from a filling product reservoir via a filling product outlet which is brought into line with the mouth of each container that is to be filled, and thereby serve to control the volume of filling product with which the container is to be filled. In order to dose the correct amount of filling product into the container, the filling device usually comprises at least one filling valve, which can be controlled via an actuator. By means of the actuator, the filling valve can be opened at a particular point in time and closed at another point in time, in order to allow the predetermined quantity of the filling product to flow into the container. The filling valves are usually disposed on a transporting device of the filling device, which is generally designed in the form of a rotary carousel, in order to enable continuous filling operation.

Various methods are known for cleaning and sterilizing the known filling devices. The cleaning-in-place (CIP) method, for example, has proved to be particularly advantageous. This method does not require the filling valves to be removed for cleaning. Instead, they are rinsed or steamed with the cleaning medium or sterilization medium while still installed. In this context it is for example known to sterilize the filling device thermally with superheated steam, and in particular to sterilize in this manner the surfaces which come into contact with the filling product. For this purpose, the filling valves are impinged with superheated steam, and in this manner brought to and maintained at the sterilization temperature. For a predetermined period, the resultant temperature of the filling valves is maintained and monitored, in order to achieve a specified sterilization effect, as known for example from DE 10 2010 031 873 A1 or DE 10 2013113621 A1.

This method of sterilization is also known as sterilization-in-place (SIP).

In order to reduce the consumption of steam while maintaining the pressure, in order to drain condensate, and in order to improve the detection of the steam throughput, a cover with a small aperture is pivoted in front of the outlet of the filling valve during the thermal sterilization, and sealingly connected with the outlet. A jet of steam then discharges through the small aperture in the cover, and its dynamic pressure is detected by means of a pressure sensor disposed beneath the cover. The temperature is determined indirectly by the measurement of the upstream pressure of the saturated steam and the steam throughput or steam pressure in the filling valve, from which the differential pressure for each filling valve is determined. In rotary devices, the pressure sensor is normally installed in a static position below the level of the cover. In this case the pressure of the jet of steam emerging from the cover is measured when the applicable valve passes across the pressure sensor.

The provision of additional devices and components such as the cover, a lifting and pivoting device for the cover, or the pressure sensor, has hygienic disadvantages, particularly if, for hygiene purposes, the filling with the filling product takes place in a filling room or clean room in the filling device, in which, relative to the environment, there is reduced microbiological contamination and/or an overpressure, and consequently the degree of sterility is higher than that of the environment. This hygienic disadvantage results from the increased necessity to clean the additional components that are installed in the clean room.

An additional method of monitoring the temperature according to the state of the art is the monitoring of each individual filling valve with a thermocouple, which is normally integrated in the filling valve or disposed on the cover. This requires, however, a separate thermocouple for each filling valve or cover, along with correspondingly elaborate wiring which, in the case of rotary machines, is installed in the rotating part.

SUMMARY OF THE INVENTION

Proceeding from the known state of the art, an object of the present invention is to provide an improved filling device for filling a container to be filled with a filling product in a filling product filling plant, and an improved method for treating a filling device.

This object is achieved by a filling device with the features of claim 1 for filling a container to be filled with a filling product in a filling product filling plant. Advantageous further developments arise from the dependent claims, the present description, and the figures.

Accordingly, a filling device for filling a container to be filled with a filling product in a filling product filling plant is proposed, comprising at least one filling valve for dosing the filling product into the container that is to be filled, as well as a sterilization device for sterilizing at least a portion of the at least one filling valve. According to the invention, a contactless temperature sensor is provided for contactlessly measuring the temperature of the filling valve.

Due to the fact that a contactless temperature sensor is provided for contactlessly measuring the temperature of the filling valve, it is possible to dispense with a cover such as is necessary in the state of the art. Consequently, the filling device can have a considerably simpler and more compact design. In addition, by this means the expense of cleaning can be reduced, since fewer components need to be cleaned, and in particular it is no longer necessary to clean parts that move relative to each other, together with their seals. This particularly applies to the cover and its displacement device.

By means of the monitoring of the temperature of the filling valve, in particular during the sterilization process, it can be ensured that at least the filling valve is impinged with the specified temperature for a predetermined period of time, in order to achieve full sterilization.

In addition, by means of the contactless temperature measurement, it is possible to avoid contamination by a contact sensor of the filling valve, and thereby of the channels through which the filling product is conveyed in the filling device. Accordingly, the device as a whole can have a more compact and hygienically more advantageous design.

The sterilization device preferably uses superheated steam for sterilization. It is however also conceivable to use any other known sterilization method in which it is necessary to maintain the surface that is to be sterilized at a specified temperature for a predetermined period of time. The contactless temperature measurement also can be advantageously employed with these sterilization processes.

The contactless measurement of the temperature can preferably be carried out on an exterior face of the filling valve, preferably in the area of a valve seat of the filling valve, so that the temperature of the filling valve can be directly measured and monitored contactlessly. When superheated steam, for example, is passed through the channels that come into contact with the filling product, and the temperature is measured at the filling valve, it can be assumed that the channels that are upstream of the filling valve will also have a temperature that is at least as high as that of the filling valve. By means of the measurement of temperature at the filling valve, it is thus possible to document and ensure the sterilization of all channels which come into contact with the filling product.

This also enables increased process reliability, since, unlike sensors which measure by contact, contactless sensors are not subject to detachment of the sensor from the surface to be measured, or wear or deformation of the sensor itself.

The contactless temperature sensor is preferably directed toward an exterior face or exterior surface of the at least one filling valve. The contactless temperature sensor preferably measures the temperature of the filling valve in the area of the valve seat. In this way the temperature of the filling valve can be measured simply and precisely.

The treatment medium for sterilization can preferably comprise steam, particularly preferably superheated steam. Alternatively, and/or in addition, the treatment medium can also comprise hydrogen peroxide or peracetic acid, preferably in combination with alcohols, particularly preferably ethanol.

In order to enable particularly precise and reliable measurement of the temperature of the at least one filling valve, in a further preferred embodiment the at least one contactless temperature sensor is designed in the form of a pyrometer and/or an infrared camera. In particular when the contactless temperature sensor is designed as an infrared camera, it can measure the temperatures of a plurality of filling valves simultaneously, so that an even simpler design of the filling device and even greater process reliability are achieved. By means of suitable evaluation software, the temperature of each filling valve can thereby be individually measured.

In a further preferred embodiment, a clean room is provided, and at least one filling product outlet of the filling valve is disposed in the clean room, wherein the at least one contactless temperature sensor is disposed outside the clean room such that it can measure the temperature of the filling valve in the clean room.

By this means, the contactless temperature sensor is, firstly, readily accessible. In other words, it is not necessary for operating or maintenance staff, for example, to enter the clean room in order to access the temperature sensor. The clean room can thus remain intact. Maintenance of the temperature sensor is therefore particularly simple despite the fact that the filling with the filling product takes place in hygienic conditions. Secondly, the risk that microbiological contamination will develop in the interior of the clean room is reduced, as is the expense of cleaning. Because the sensor system for measurement of the temperature of the valve seat is disposed outside the clean room, contamination of the sensor system by splashes of filling product is further prevented. Such contamination could otherwise lead in turn to impairments in the measurement results from the temperature sensor.

In order to enable particularly efficient filling with the filling product, the at least one filling valve can be disposed on a transport device, preferably a rotary carousel.

In a further preferred embodiment, fewer contactless temperature sensors than filling valves are provided, and preferably a single contactless temperature sensor is provided for contactlessly measuring the temperature of all filling valves, wherein filling valves are displaceable relative to the contactless temperature sensor, wherein preferably the temperature of the filling valve can be measured as the at least one filling valve moves past the at least one contactless temperature sensor.

Due to the fact that fewer contactless temperature sensors than filling valves are provided, the expense of temperature measurement can be reduced. This is particularly apparent when only a single temperature sensor is used for the entire filling device. It is nevertheless possible to carry out reliable measurement of the temperatures of all filling valves because the filling valves are moved past the temperature sensor.

In this case, the contactless temperature sensor is preferably disposed in a fixed position, so that it can also be connected particularly easily with a device for processing the measured temperature value, preferably a control and/or regulation unit, and in particular it is unnecessary to transfer the applicable signal from a rotating component to a stationary component. It is furthermore possible, particularly in the case of filling devices with a rotary design, to monitor a plurality of filling devices that are disposed on the rotary carousel. The temperature of the individual filling valves can be measured as each filling valve is moved past the temperature sensor, i.e. moved through its measurement zone. The filling device can then have a particularly simple design. In addition, both the susceptibility to faults and the complexity of the filling device are reduced, since only one sensor needs to be provided, by means of which the temperature of a plurality of filling valves can be monitored.

In a further preferred embodiment, a plurality of filling valves are provided, wherein the plurality of filling valves are preferably disposed on a transport device, and a separate contactless temperature sensor is assigned to each filling valve. By this means the temperature of each filling valve can be measured particularly precisely. In addition, this enables permanent measurement and thus permanent monitoring of the temperature of the filling valve, so that a cleaning and/or sterilization procedure can take place in a particularly reliable manner. It can also be ensured by this means that the temperature of each individual filling valve is measureable at any time, and it is thus possible to achieve particularly precise monitoring and control and/or regulation of the treatment process.

Particularly efficient filling with the filling product can be achieved if a plurality of filling valves are provided, wherein the plurality of filling valves are preferably disposed on the transport device. By this means a plurality of containers that are to be filled can be filled substantially simultaneously by the plurality of filling valves.

In a further preferred embodiment, a control and/or regulation unit for the treatment process, connected with the at least one contactless temperature sensor, is provided, which controls and/or regulates the treatment of the at least one filling valve using the temperature value of the at least one filling valve that is measured by the at least one contactless temperature sensor. By this means a particularly efficient and resource-saving sterilization can be achieved, since the quantity of steam that needs to be supplied can be regulated precisely according to the temperature, and excessive consumption of steam can thereby be avoided.

Treatment medium can also be saved if, as in a preferred further embodiment, the control and/or regulation unit is configured such that the at least one filling valve is opened during the treatment process when the temperature value of the filling valve, as measured by the contactless temperature sensor, falls below a specified temperature value. It is then also possible to discharge any condensate that may have arisen due to the fall in temperature, preferably by blowing it out. In addition, the interior of the filling valve, including the outlet of the filling valve and the interior surface of the base piece of the filling valve, with any centering bell that may be arranged on the outlet of the filling valve, can be rinsed with treatment medium or impinged with steam sufficiently long for the temperature of the filling valve again to rise above the specified temperature value, and/or sufficiently long for the condensate to be discharged.

Particularly preferably, the opening and closing of the filling valve alternate. The filling valve is opened or closed depending on the measured temperature value. In other words, the filling valve is switched at intervals which are temperature-dependent. Accordingly, treatment medium is only discharged via the open filling valve when it is needed in order to heat the valve and/or discharge condensate.

The object described above is further achieved by a method with the features of claim 8 for sterilizing at least a portion of at least one filling device in a filling product filling plant. Advantageous further developments of the method arise from the dependent claims, the present description and the figures.

Accordingly, a method for sterilizing at least a portion of at least one filling valve in a filling product filling plant is proposed, comprising the impingement of the at least one filling valve with a sterilization medium. According to the invention, the temperature of the at least one filling valve is measured contactlessly.

Due to the fact that the temperature of the at least one filling valve is measured contactlessly, the advantages that have already been mentioned in connection with the filling device can be attained.

In a further preferred embodiment, a clean room is provided, and at least one filling product outlet of the filling valve is disposed in the clean room, and the temperature of the at least one filling valve is measured outside the clean room.

In this manner a hygienically advantageous design of the plant and the method can be achieved.

It can further be advantageous if the sterilization of the at least one filling valve is controlled and/or regulated using the contactlessly measured temperature value of the at least one filling valve.

It is thereby possible to achieve an efficient and reliable execution of the sterilization process, which can also reduce the operating costs, since the sterilization medium, and in particular the superheated steam, can be used in only the quantities that are necessary at the particular point in time.

In a preferred further development, the at least one filling valve is opened during the sterilization process when the contactlessly measured temperature value of the filling valve falls below a specified temperature value.

By this means, treatment medium can be saved. In addition, any condensate that may have arisen due to the fall in temperature is discharged, and the interior of the filling valve, including the outlet of the filling valve and the interior face of the base piece of the filling valve, with any centering bell that may be arranged on the outlet of the filling valve, can be rinsed with treatment medium or impinged with steam sufficiently long for the temperature of the filling valve again to rise above the specified temperature value, or sufficiently long for the condensate to be discharged. Preferably, the filling valve is repeatedly opened and closed alternately, at intervals which are temperature-dependent. In other words, the filling valve is opened when the measured temperature value falls below the specified temperature value, and closed again when the temperature value is again above the specified temperature value. Treatment medium is therefore only discharged via the open filling valve when it is needed in order to heat the valve and/or discharge condensate.

Alternatively, in order to simplify the control and/or regulation, when the temperature is below the specified value the filling valve can simply be opened for a predetermined time period.

BRIEF DESCRIPTION OF THE FIGURES

Preferred further embodiments of the invention are more fully explained by the description below of the figures. The figures show.

DETAILED DESCRIPTION OF EXAMPLES OF PREFERRED EMBODIMENTS

Examples of preferred embodiments are described below with the aid of the figures. In the figures, elements which are identical or similar, or have identical effects, are designated with identical reference signs. In order to avoid redundancy, repeated description of these elements is in part dispensed with.

Figure 1:
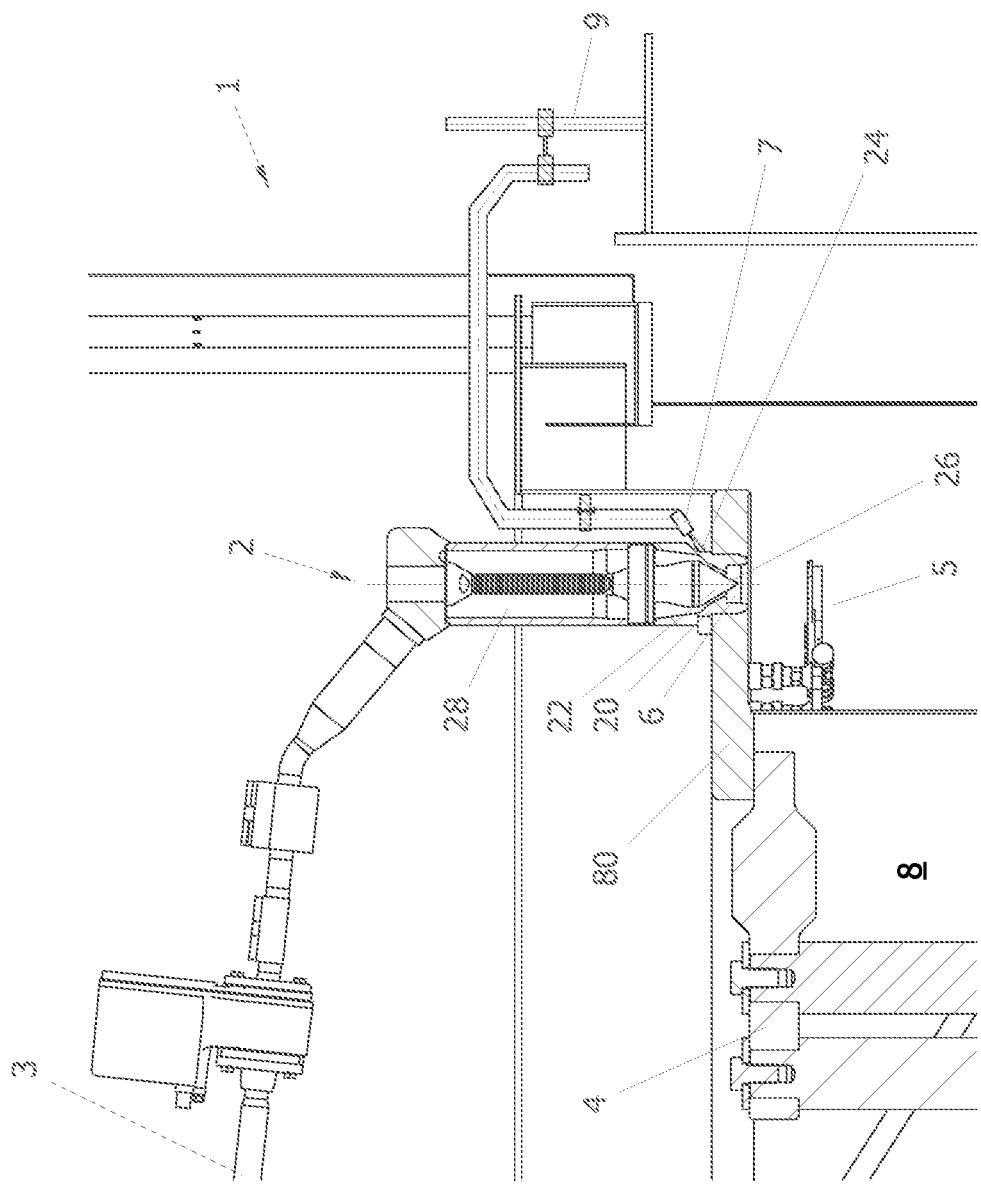
FIG. 1 a schematic sectional view of a filling device for filling a container to be filled with a filling product in a filling product filling plant.

FIG. 1 shows schematically a sectional view of a filling device 1 for filling a container to be filled with a filling product in a filling product filling plant. The filling device 1 is designed as a rotary device, and has a rotatable carousel 4 and a stationary part 9 that is stationary relative to the rotary carousel 4.

A clean room 8 is also provided, in which the container is filled with the filling product in a controlled atmosphere. The clean room 8 is enclosed, or formed, by a clean room cover 80 which is formed on the rotary carousel 4 and by clean room walls (which are not shown in the figures).

A plurality of filling valves 2 are disposed on the periphery of the rotary carousel 4, in order to produce in the filling product filling plant a continuous stream of filled containers on the rotary carousel 4.

The filling valves 2 pass through the clean room cover 80 such that only their filling product outlet 26 and filling valve base piece 6 issue into the clean room 8. The filling valve base piece 6 can alternatively be designed as a centering bell if containers are filled while pressed on.

A plurality of container receptacles 5 are disposed beneath the filling valves 2 to accommodate the containers that are to be filled, with one container receptacle 5 assigned to each filling valve 2. Each filling valve 2 is connected via a product supply line 3 with a medium distributor. Via the medium distributor (which is not shown here), the filling product is supplied from a product reservoir and a treatment medium in the form of superheated steam is supplied from a sterilization device.

Above its filling product outlet 26, in the interior 28 of the valve, each filling valve 2 has a valve cone 22, which is displaceable in the direction of the longitudinal axis of the filling valve 2, and can be lowered into a valve seat 20 in a sealing manner in order to close the filling valve 2. To open the filling valve 2, the valve cone 22 is lifted out of the valve seat 20, such that between the valve cone 22 and the valve seat 20 an annular gap is formed, through which the filling product or a treatment medium can reach the filling product outlet 26 and discharge therefrom.

On the stationary part 9, a temperature sensor 7 is disposed, which can determine in a contactless manner the temperature of a filling valve 2 that moves past it. The contactless temperature sensor 7 is provided in a fixed position on the filling device 1. It is positioned such as to measure the temperature of the filling valve 2 on an exterior face 24 of the filling valve 2 in the region of the valve cone 20.

The contactless temperature sensor 7 is configured such that it can determine the temperature of, in each case, one of the plurality of filling valves 2 as they move past the contactless temperature sensor 7. In other words, the contactless temperature sensor 7 can distinguish between the temperatures of the individual filling valves 2. The contactless temperature sensor 7 is thereby capable of successively measuring the individual temperatures of each of the filling valves 2 that are moved past it as the rotary carousel 4 rotates.

The contactless temperature sensor 7 is further connected with a control and/or regulation unit (not shown in the figures), by means of which the treatment, for example the sterilization, of the filling valves 2 can be controlled and/or regulated, and by means of which the temperature of the filling valves 2 can be monitored.

The contactless temperature sensor 7 is designed, for example, as an infrared camera. Alternatively, it can be designed as a pyrometer or in the form of a different type of contactless temperature sensor.

For the purpose of cleaning or thermal sterilization of the filling valves 2, steam is supplied via the product supply lines 3 to the filling valves 2. In order to achieve adequate impingement of the contact surfaces of the valve cone 22 and the valve seat 20, the filling valves 2 are preferably initially held in an open position. In order to keep the consumption of sterilization steam as low as possible, the filling valve 2 is subsequently partially or fully closed, so that the sterilization steam is primarily present in the valve interior 28. Alternatively, a cover or sterilization cap can be disposed in front of the filling product outlet 26, in order to achieve a defined volume flow of the sterilization medium.

If the contactlessly measured temperature value of a particular filling valve 2 falls below a specified temperature value, the applicable filling valve 2 is opened so that any condensate that may have arisen due to the fall in temperature is discharged from the valve interior 28, and fresh superheated steam is supplied to heat the filling valve 2.

It has proved to be particularly advantageous to alternately open and close the filling valve 2, wherein the intervals at which the filling valve 2 is switched are based on the measured temperature values, and are hence temperature-dependent. Thus treatment medium is only discharged via the opened filling valve when this is necessary in order to heat the filling valve 2 and/or discharge condensate. In this manner, the consumption of treatment medium can be reduced.

Figure 2:
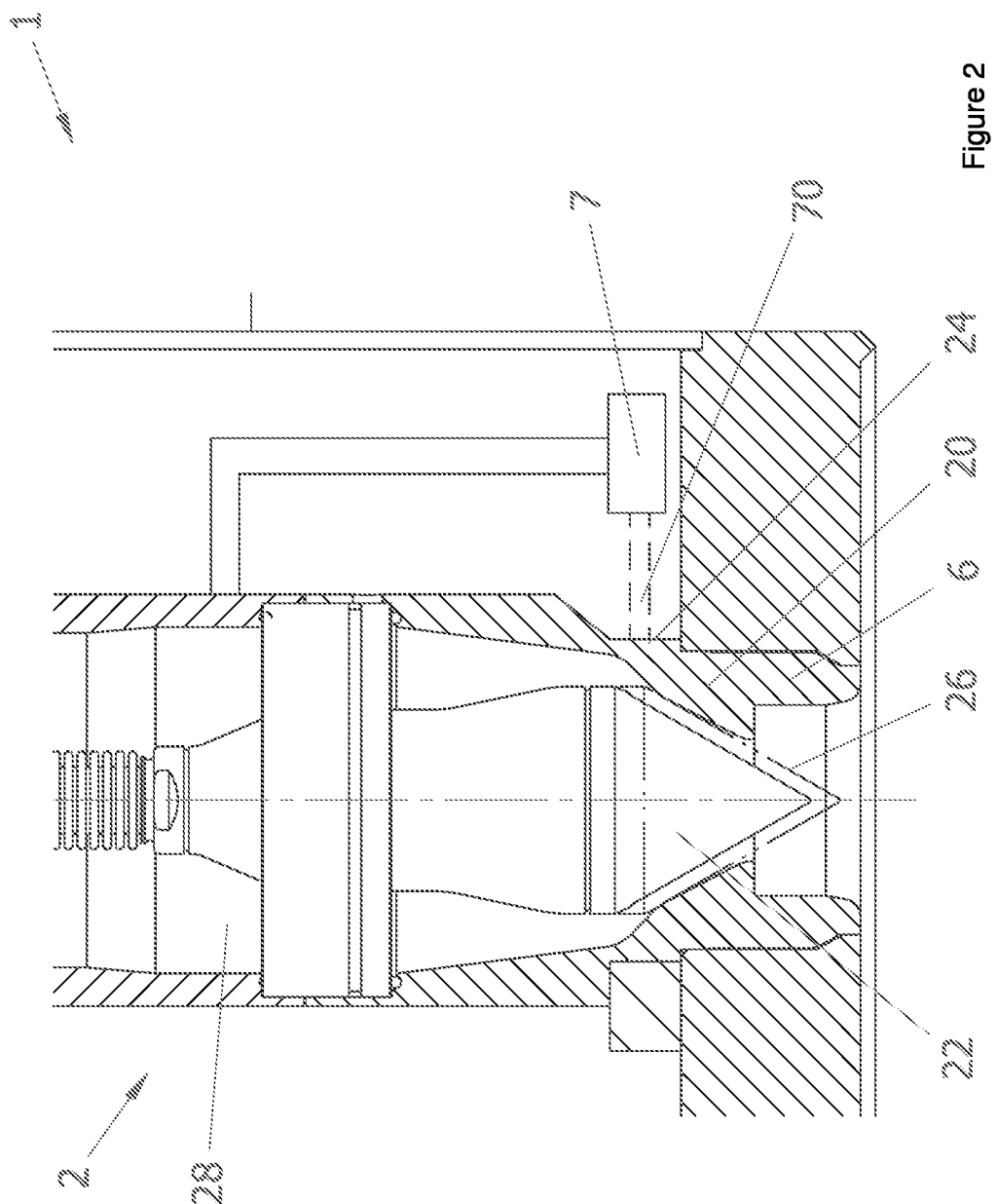
FIG. 2 a schematic detailed sectional view of a filling valve of a filling device for filling a container to be filled with a filling product, in an alternative embodiment.

FIG. 2 shows schematically a detailed sectional view of a filling valve 2 of a filling device 1 for filling a container to be filled with a filling product, in an alternative embodiment. The filling device 1 that is shown here corresponds substantially to that shown in FIG. 1. In contrast to the filling device 1 shown in FIG. 1, however, in the embodiment shown in FIG. 2 a contactless temperature sensor 7 is disposed on each of the plurality of filling valves 2. The temperature sensors 7 are thus provided on the rotating part, i.e. on the rotary carousel 4.

In this embodiment, the contactless temperature sensors 7 are designed as pyrometers. Alternatively, other types of contactless temperature sensor can also be used.

The filling valve 2 is designed such that the contactless temperature sensor 7 measures the temperature of the filling valve 2 in the area of the valve seat 20, on an exterior face 24 of the filling valve 2. The measuring beam of the pyrometer is indicated by the reference sign 70.

In accordance with common practice, the various features illustrated in the drawings may not be drawn to scale. The illustrations presented in the present disclosure are not meant to be actual views of any particular apparatus (e.g., device, system, etc.) or method, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, it is understood that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

To the extent applicable, all individual features that are described in the individual example embodiments can be combined with each other and/or exchanged, without departing from the field of the invention.

The invention claimed is:

1. A filing device for filling a container to be filled with a filling product in a filling product filling plant, the filing device comprising:
    a clean room;
    at least one filling valve that includes at least one filling product outlet, the filling value configured to dose the filling product into the container that is to be filled and the at least one filling product outlet being disposed in the clean room;
    a sterilization device configured to sterilize at least a portion of the at least one filling valve; and
    a contactless temperature sensor disposed outside the clean room and configured to contactlessly measure the temperature of the at least one filling product outlet of the at least one filling valve in the clean room.

2. The filing device according to claim 1, wherein the contactless temperature sensor is designed in the form of a pyrometer and/or an infrared camera.

3. The filing device according to claim 1, wherein the contactless temperature sensor is disposed outside of the at least one filling valve.

4. The filing device according to claim 1, further comprising a transport device upon which the at least one filling valve is disposed.

5. The filing device of claim 4, wherein the transport device is a rotary carousel.

6. The filing device according to claim 1, further comprising a plurality of filling valves that include the at least one filling valve and a plurality of contactless temperature sensors that include the contactless temperature sensor, wherein a number of the plurality of contactless temperature sensors is less than a number of the plurality of filling valves.

7. The filing device according to claim 6, further comprising a control unit connected with the plurality of contactless temperature sensors and the sterilization device, the control unit configured to control the sterilization of the plurality of filling valves by the sterilization device using the temperature of the plurality of filling valves that are measured by the plurality of contactless temperature sensors.

8. The filing device according to claim 1, further comprising:
    a plurality of filling valves that include the at least one filling valve; and
    a plurality of contactless temperature sensors that include the contactless temperature sensor, wherein the plurality of filling valves are disposed on a transport device, and a separate one of the plurality of contactless temperature sensors is assigned to each one of the plurality of filling valves.

9. The filing device according to claim 1, further comprising a control unit connected with the contactless temperature sensor and the sterilization device, the control unit configured to control the sterilization of the at least one filling valve by the sterilization device using the temperature of the at least one filling valve that is measured by the contactless temperature sensor.

10. The filing device of claim 1, further comprising a plurality of filling valves that include the at least one filling valve that are displaceable relative to the contactless temperature sensor, wherein the contactless temperature sensor is a single contactless temperature sensor that is configured to contactless measure the temperature of each of the plurality of filling valves.

11. The filing device of claim 10, further comprising a transport device configured to move the plurality of filling valves pass the contactless temperature sensor, wherein the contactless temperature sensor is configured to contactlessly measure the temperature of each of the plurality of filling valves as each of the plurality of filling valves move pass the contactless temperature sensor.

12. The filing device of claim 1, further comprising a transport device upon which the at least one filling valve is disposed.

13. The filing device according to claim 3, further comprising a control unit connected with the contactless temperature sensor and the sterilization device, the control unit configured to control the sterilization of the at least one filling valve by the sterilization device using the temperature of the at least one filling valve that is measured by the contactless temperature sensor.

14. A method for sterilizing at least a portion of at least one filling valve in a filling product filling plant, the method comprising:
    impinging the at least one filling valve with a sterilization medium during a sterilization process; and
    contactlessly measuring the temperature of the at least one filling valve during the sterilization process, wherein a filling product outlet of the filling valve is disposed in a clean room, and the temperature of the at least one filling valve is contactles sly measured outside the clean room.

15. The method according to claim 14, wherein contactlessly measuring the temperature is performed by a contactless temperature sensor disposed outside of the at least one filling valve.

16. The method according to claim 14, wherein the impinging of the at least one filling valve with the sterilization medium is controlled using the contactlessly measured temperature of the at least one filling valve.

17. The method according to claim 14, further comprising opening the at least one filling valve during the sterilization process when the contactlessly measured temperature of the at least one filling valve falls below a specified temperature value.

18. The method according to claim 15, wherein the impinging of the at least one filling valve with the sterilization medium is controlled using the contactlessly measured temperature of the at least one filling valve.

19. The method according to claim 18, further comprising opening the at least one filling valve during the sterilization process when the contactlessly measured temperature of the at least one filling valve falls below a specified temperature value.

20. The method according to claim 15, further comprising opening the at least one filling valve during the sterilization process when the contactlessly measured temperature of the at least one filling valve falls below a specified temperature value.

* * * * *